(12) United States Patent
Godfrin

(10) Patent No.: US 10,273,444 B2
(45) Date of Patent: Apr. 30, 2019

(54) LYSIS/RESEALING PROCESS AND DEVICE FOR INCORPORATING AN ACTIVE INGREDIENT, IN PARTICULAR ASPARAGINASE OR INOSITOL HEXAPHOSPHATE, IN ERYTHROCYTES

(71) Applicant: ERYTECH PHARMA, Lyons (FR)

(72) Inventor: Yann Godfrin, Lyons (FR)

(73) Assignee: ERYTECH PHARMA, Lyons (FR)

( * ) Notice: Subject to any disclaimer, the term of this patent is extended or adjusted under 35 U.S.C. 154(b) by 0 days.

(21) Appl. No.: 14/089,834

(22) Filed: Nov. 26, 2013

(65) Prior Publication Data

US 2014/0154797 A1    Jun. 5, 2014

Related U.S. Application Data

(62) Division of application No. 11/573,093, filed as application No. PCT/IB2005/002323 on Aug. 4, 2005, now Pat. No. 8,617,840.

(30) Foreign Application Priority Data

Aug. 5, 2004   (FR) ..................... 04 08667

(51) Int. Cl.
*A61K 9/50*      (2006.01)
*C12M 1/00*      (2006.01)
*A61K 35/18*     (2015.01)
*A61K 31/6615*   (2006.01)

(52) U.S. Cl.
CPC .......... *C12M 47/06* (2013.01); *A61K 9/5068* (2013.01); *A61K 31/6615* (2013.01); *A61K 35/18* (2013.01)

(58) Field of Classification Search
CPC ...... C12M 47/06; A61K 9/5068; A61K 35/18; A61K 31/6615
See application file for complete search history.

(56) References Cited

U.S. PATENT DOCUMENTS 4,652,449 A * 3/1987 Ropars et al. ................ 424/533
4,801,777 A * 1/1989 Auerbach ..................... 219/687

* cited by examiner

*Primary Examiner* — Gautam Prakash
(74) *Attorney, Agent, or Firm* — B. Aaron Schulman, Esq.; Stites & Harbison, PLLC

(57) ABSTRACT

A lysis/resealing process for preparing erythrocytes containing active ingredient is provided comprising placing a globular concentrate in suspension in an isotonic solution having a haematocrit level which is equal to or greater than 65%, with refrigeration at 1 to 8° C.; measuring the osmotic fragility based on a sample of erythrocytes from that same globular concentrate, preferably on a sample of the suspension; lysis and internalization procedure of the active ingredient, inside the same chamber, at a temperature maintained at 1 to 8° C., comprising allowing the erythrocyte suspension having a haematocrit level equal to or greater than 65% and a hypotonic lysis solution which is refrigerated at 1 to 8° C., to circulate in a dialysis cartridge; the lysis parameters being adjusted in accordance with the osmotic fragility previously measured; and resealing in a second chamber at a temperature of from 30 to 40° C. by means of a hypertonic solution.

19 Claims, 4 Drawing Sheets

LYSIS/RESEALING PROCESS AND DEVICE FOR INCORPORATING AN ACTIVE INGREDIENT, IN PARTICULAR ASPARAGINASE OR INOSITOL HEXAPHOSPHATE, IN ERYTHROCYTES

CROSS-REFERENCE TO RELATED APPLICATIONS

This application is a divisional application of U.S. application Ser. No. 11/573,093, having a filing date of Feb. 11, 2008, now U.S. Pat. No. 8,617,840, issued Dec. 31, 2013, which was a 371 application of PCT/IB2005/002323, filed Aug. 4, 2005, all of said applications being incorporated herein by reference.

FIELD OF THE INVENTION

The present invention relates to a process which allows the so-called lysis/resealing technique to be carried out, which allows active ingredients to be incorporated in erythrocytes. The invention also relates to a device which can carry out that process.

The invention further relates to erythrocyte compositions which contain asparaginase or the like, or inositol hexaphosphate, and which can be obtained by carrying out the process according to the invention.

BACKGROUND OF THE INVENTION

The lysis/resealing technique is described in patents EP-A-101 341 and EP-A-679 101. The latter describes a relatively complex installation which comprises, firstly, a refrigerated housing for the lysis portion, in which there is placed an assembly comprising single-use elements, including a dialysis cartridge, tubes, chicane type or serpentine pouches and removable metal elements, such as a serpentine cooling arrangement, and, secondly, a housing for the resealing, which housing is provided with reheating means and in which a single-use assembly of plastics material is placed.

The red corpuscles, which have been separated from the plasma beforehand and which are subjected to weak ion forces (in a hypotonic medium), swell until they reach a critical volume, at which the membrane is distended to the point of becoming permeable to ions and macromolecules. Examination under a microscope of the erythrocyte membranes then reveals the appearance of pores which measure from 20 to 500 nm, as a result of which haemoglobin may escape (P. Seeman J. Cell. Biol. 1967, 32(1): 55-70). Restoration of the isotonicity of the suspension medium brings about closure of the pores, making the membrane impermeable to macromolecules. Only permeability to ions is maintained.

The hypotonic shock is brought about by causing the red corpuscles to circulate in the «blood» compartment of a dialyser, preferably having hollow fibres, and causing a hypotonic solution to circulate in counter-current in the «dialysate» compartment. The advantage of this technique resides in the confinement of the red corpuscles during the hypotonic shock, which allows losses of constituents which are essential to the life of those cells to be considerably reduced. Thus, the half-life of the red corpuscles is not significantly modified in vivo.

The advantage of using red corpuscles as vehicles for medicaments, in comparison with other techniques, such as encapsulation in liposomes or microspheres, resides substantially in that those corpuscles have «natural» biocompatibility, are completely biodegradable according to a well-known process, have a relatively long in vivo life expectancy (approximately 120 days) and in that various chemical and therapeutic molecules can be encapsulated therein.

The process of internalisation by lysis and resealing of the erythrocytes is a complex multi-factor phenomenon. Some significant physical/chemical parameters which have a bearing on the variability of the results are the concentration in terms of haemoglobin before dialysis, the flow rate of the erythrocyte suspension in the dialyser, the osmolarity of the buffer of hypotonic dialysis, the dialysis temperature and resealing temperature and the trans-membranous pressure in the dialyser. The osmotic fragility of the erythrocytes varies from one blood sample to the next and could be a leading biological factor. Thus, L. Boucher et al., Biotechnol. Appl. Biochem. 1996, 24, 73-78, studied the influence of the variations in the osmotic fragility of various populations of red corpuscles on the distribution and final concentration of inositol hexaphosphate. In conclusion, the authors indicate that the initial osmotic fragility of the red corpuscles has a predominant role in terms of the degree of lysis and the variations in internalisation of the active ingredient, and that that osmotic fragility depends on a number of factors, such as the permeability of the red corpuscles, the relationship between surface-area/volume and ion content, the physiological state and age of the donor (see also A. A. Hussain et al., Br. J. Haematol. 1984, 57(4): 716-718), the length of time the blood is stored, the presence of medicaments, illnesses (see also K. Kolanjiappan et al., Clin. Chim. Acta 2002, 326(1-2): 143-149) and treatments. The results obtained, with the flow rate of the erythrocyte suspension being caused to vary, demonstrated the extreme sensitivity of the operating conditions, with a flow rate of from 12 to 14 ml/min depending on whether the red corpuscles belong to a group having a low level of fragility or a group having a high level of fragility.

Therefore, those texts provide initial information on the various factors which influence the osmotic fragility of the red corpuscles and the effectiveness of incorporation by means of the lysis/resealing technique. They allow an understanding of the difficulties encountered in practice, which explain that that technique cannot be applied routinely in human health care.

A quite recent publication summarises the current situation very well. C. G. Millan et al. published, in Journal of Controlled Release 2004, 95: 27-49, a general review of the use of erythrocytes as pharmaceutical vehicles, in which they conclude that, in spite of the interest which they are exciting in human medicine, their development is still very limited today because of the difficulties of storage, risks of contamination and absence of a proven industrial procedure allowing the preparation thereof.

Asparaginase is an enzyme produced from bacterial microorganisms (*E. Coli* or *Erwinia*) which hydrolyses and depletes asparagine, an amino acid which is indispensable for synthesising the proteins necessary for cell life, in particular fibroblasts. Some cancerous lymphoblastic cells do not have, unlike normal cells, the capacity to synthesise their asparagine themselves and are dependent on extracellular sources. Treatment by asparaginase therefore deprives them of that constituent, leading to their death. This antimitotic is selective with respect to tumour cells.

In humans, however, native asparaginase induces the production of antibodies which are present in more than 70% of patients on average, leading to an increase in the clearance of asparaginase and allergic reactions which are sometimes very severe (B. Wang et al., Leukaemia 2003 17, 8: 1583-1588). Thus, although asparaginase is very effective in the treatment of acute lymphoblastic leukaemias, it is highly toxic and may lead to hypersensitivity reactions, ranging from a simple reaction of the urticary type to a full-blown anaphylactic shock. Furthermore, there are observed detrimental effects of the neurological type (disturbances to consciousness), haemostatic type (hypofibrinogenaemia, reduction in the serum level of antithrombin III and other coagulation factors, leading to haemorrhagic and/or thrombotic complications), gastro-intestinal type and pancreatic type (including acute inflammations of the pancreas).

The encapsulation of asparaginase in erythrocytes allows the therapeutic index to be improved (D. Schrijvers et al., Clin. Pharmacokinet. 2003, 42 (9): 779-791). Therefore, it would be extremely advantageous to provide a process which allows asparaginase to be encapsulated in erythrocytes in a reproducible and industrial manner.

Furthermore, inositol hexaphosphate has been proposed as a substitute for 2,3-DPG (2,3-diphosphoglycerate) in erythrocytes in order to significantly reduce the affinity of oxygen for haemoglobin and to increase the release of oxygen in tissues (EP-A-0 101 341). U.S. Pat. No. 4,321, 259, U.S. Pat. No. 5,612,207 and U.S. Pat. No. 6,610,702 describe the incorporation of that substitute in erythrocytes and the use thereof in various therapeutic applications. They include an indication as an additive for a cancer treatment by means of radiotherapy, in order to improve the oxygenation of hypoxic tumours and their sensitivity to radiotherapy. However, that indication is not accompanied by any feasibility element.

For encapsulation, U.S. Pat. No. 4,321,259 uses the fusion between erythrocytes and liposomes which contain inositol hexaphosphate. U.S. Pat. No. 5,612,207 uses a technique by electroporation. U.S. Pat. No. 6,610,702 sets out an improvement in the electroporation technique, by inositol hexaphosphate being associated with ammonium cations in order to form a biocompatible hydrosoluble complex which can promote introduction in erythrocytes. Finally, in Biotechnol. Appl. Biochem. 1996, 24, 73-78, described above, L. Boucher et al. study the introduction of inositol hexaphosphate in erythrocytes by the lysis/resealing technique. Therefore, various routes are available to the person skilled in the art in order to introduce that compound into erythrocytes. As C. G. Millan et al. (above), mentions, when making reference to inositol hexaphosphate for the transport of oxygen in general, however, the use of erythrocytes incorporating a molecule such as inositol hexaphosphate nowadays encounters the absence of a proven industrial procedure.

SUMMARY OF THE INVENTION

In this application, therefore, it would be very advantageous to have a process which allows inositol hexaphosphate to be encapsulated in erythrocytes in a reproducible and industrial manner.

DETAILED DESCRIPTION OF THE PREFERRED EMBODIMENTS

Taking the above into consideration, the problem addressed by the applicant is to provide a process for industrial lysis/resealing which allows erythrocytes to be produced incorporating desired quantities of active ingredient in a reproducible manner, and allowing a product to be obtained which complies with the standards for blood transfusion (sterility, absence of pathogens and pyrogens).

An important object of the invention is to provide such a process which can be applied to globular concentrates which comply with the standards required for blood transfusion.

Another object is to provide such a process which allows asparaginase or inositol hexaphosphate to be encapsulated in erythrocytes in an effective, reproducible, reliable and stable manner.

These objects, as well as others, are achieved by a lysis/resealing process for preparing erythrocytes containing at least one active ingredient, the process comprising the following steps:

1—placing a globular concentrate in suspension in an isotonic solution having a haematocrit level which is equal to or greater than 65%, with refrigeration at from +1 to +8° C., 2—measuring the osmotic fragility based on a sample of erythrocytes from that same globular concentrate, the steps 1 and 2 being able to be carried out in any order (including in parallel), 3—lysis and internalisation procedure of the active ingredient, inside the same chamber, at a temperature which is constantly maintained at from +1 to +8° C., comprising allowing the erythrocyte suspension having a haematocrit level which is equal to or greater than 65% and a hypotonic lysis solution which is refrigerated at from +1 to +8° C., to circulate in a dialysis cartridge; the lysis parameters being adjusted in accordance with the osmotic fragility measured previously; and 4—resealing procedure carried out in a second chamber, inside which the temperature is adapted to the resealing, preferably from +30 to +40° C., and in the presence of a hypertonic solution.

In the preferred embodiment, step 2 is carried out on a sample of the suspension prepared in step 1. As it will be explained thereafter, the suspension may have been prepared from a globular concentrate that has been subjected to usual processing operations such as washing with a saline solution. Moreover, the active ingredient to be internalized may be present in this suspension. Therefore, it is advantageous to carry out step 2 on a sample of this suspension and in the case the active ingredient is in the initial suspension, step 2 is carried out on a sample of suspension containing the active ingredient.

The term «internalisation» is intended to refer to the introduction of the active ingredient inside the erythrocytes.

According to a feature of the invention, the globular concentrate is suspended in an isotonic solution having a high haematocrit level which is equal to or greater than 65%, and preferably equal to or greater than 70%, and that suspension is refrigerated at from +1 to +8° C., preferably from +2 to +6° C., typically in the order of +4° C. According to a particular method, the haematocrit level is from 65 to 80%, preferably from 70 to 80%.

In accordance with an important feature of the invention, the osmotic fragility is measured relative to the erythrocytes shortly before the lysis step. The erythrocytes or the suspension containing them are advantageously at a temperature near to or identical to the temperature selected for lysis. According to another advantageous feature of the invention, the measurement of the osmotic fragility carried out is rapidly used, that is to say that the lysis procedure is carried out a short time after the sample is taken. Preferably, that time interval between the sample being taken and the start of lysis is less than or equal to 30 minutes, still more preferably less than or equal to 25 minutes, or even to 20 minutes.

The two parameters which allow the dialysis to be controlled are the time for which the cells are present in the dialyser (in accordance with the characteristics thereof) and the osmolarity of the dialysate. The two parameters must be adjusted in accordance with the characteristics of osmotic strength, or conversely osmotic fragility, of the red corpuscles which are processed in order to be subjected to the lysis/resealing steps. That osmotic strength can be characterised by at least one of the following parameters:

a. the osmolarity of the medium for which haemolysis appears, that is to say, the start of the formation of the pores.
b. The velocity V of haemolysis, which is established by the gradient of the linear portion of the haemolysis %=f (osmolarity of the medium) curve.
c. The percentage of haemolysis for a given osmolarity.
d. The osmolarity which allows 50% haemolysis ($H_{50}$) to be obtained.
e. The time for obtaining a given percentage of haemolysis (for example, 50%).

According to preferred embodiments, the osmotic strength is characterised by means of the parameters b, d or b and d.

Therefore, the osmotic fragility must be measured within a short period of time, which is compatible with the short time interval between the sample being taken and the start of lysis. In accordance with a feature of the invention, one or more of those haemolysis parameters is measured, against a hypotonic solution, having known isotonicity, for example, water (distilled water or the like), through a semi-permeable membrane. A manual method may be envisaged. In accordance with a preferred embodiment of the invention, however, the osmotic fragility is measured by means of an automatic measuring device which is configured to measure the osmotic fragility of a sample of erythrocytes in less than 15 minutes, more particularly in less than 12 minutes and preferably in less than 10 minutes, and the result obtained is used within a brief period of time in order to adjust the lysis parameters and to start the lysis.

The measurement of the osmotic fragility may be carried out by means of a device which at least partially automates the manual technique described by J. V. Dacie in Practical Haematology, $2^{nd}$ edn, Churchill, London 1956. An example of such a device is described in the article by J. Didelon et al., Clinical Hemorheology and Microcirculation 23 (2000) 31-42. The principle is based on the use of a device which brings together, at one side and the other of a semi-permeable membrane, the sample of the erythrocyte suspension to be evaluated, and a hypotonic solution, having known isotonicity, for example, distilled water, in suitable volumes, so as to generate slow haemolysis of the erythrocytes as the NaCl ions diffuse towards the solution, for example, distilled water. The progress of haemolysis over time is followed by a measurement of the transmittance (see also J. Didelon et al., Biorheology 37, 2000: 409-416) by means of a laser beam which has a wavelength of 808 nm. A photoelectric cell measures the variations in the light transmitted through the suspension. For example, the measurements are carried out over 10 minutes. The device allows one or more of the parameters a-e mentioned above to be obtained.

According to a first method, the measurement of the osmotic fragility is carried out on a sample whose initial temperature is from +1 to +8° C., preferably with distilled water which is also at that temperature, under conditions in which the change in the temperature isn't detrimental to the measurement. In accordance with a second method, the measurement of the osmotic fragility is carried out on a sample which is maintained at the temperature of from +1 to +8° C. Thus, the measurement device described in J. Didelon et al. above may be modified in order to allow the temperature to be controlled. Preferably, this temperature is similar or identical to the lysis temperature.

Once one or more of those parameters has/have been determined, a relationship can be applied taking into consideration the parameter(s) in order to establish either the flow rate of the cells in the dialyser, or the osmolarity of the dialysate, which is sufficient to obtain red corpuscles which encapsulate the «active» substance and/or the desired quantity thereof:

$$\text{Flow rate of erythrocytes}=[A\times(H_{50})]+[B\times(V)]+K$$

A and B=variables which are adjustable in accordance with the dialyser and osmolarity of the lysis solution
K=adjustment constant.

$$\text{Osmolarity of dialysate}=[C\times(H_{50})]+[D\times(V)]+K$$

C and D=variables which are adjustable in accordance with the dialyser and the flow rate of erythrocytes in the dialyser
K=adjustment constant.

According to a preferred embodiment, the concentration of NaCl in g/L which brings about 50% haemolysis is measured (parameter d.) and the flow rate of the erythrocyte suspension in the dialysis cartridge is adjusted in accordance with the measured concentration values.

According to an aspect of the invention, the lysis procedure is started when the temperature of the erythrocyte suspension is from +1 to +8° C., and the osmotic fragility has been measured and the lysis parameters recorded.

According to an advantageous feature, the initial suspension to be processed is placed in the lysis/internalisation chamber mentioned above. According to an embodiment of the invention, the process uses a refrigerated module which is provided with temperature control, a pouch of the erythrocyte suspension which is refrigerated at from +1 to +8° C. is placed in that module and is connected, or is to be connected, to a sterile single-use removable assembly which comprises a dialysis cartridge, tubes for connecting the cartridge, at one side, to the pouch and, at the other side, to the lysis solution, the module further comprising means which can bring about the circulation of the erythrocyte suspension and the lysis solution, inside which module the temperature is stabilised at from +1 to +8° C. The refrigerated module has dimensions so as to accommodate the pouch and the removable single-use assembly. The fact that the pouch, the dialysis cartridge, the lysis solution, which are connected by the various tubes, are provided in a single refrigerated module of this type is an advantageous feature of the process according to the invention.

The term «pouch» refers to the flexible pouches which are commonly used in the field of blood transfusions and blood derivatives.

According to an important aspect of the invention, steps are taken to keep the erythrocytes in homogeneous suspension in the pouch so as to keep stable the haematrocrit level of the suspension passing through the dialyser. In accordance with a feature of the invention, the pouch is thus provided with external loop type circulation which can bring about circulation of the suspension to and from the pouch.

The term dialysis cartridge is intended to refer to an element which comprises two compartments which are separated by a dialysis wall, through which ion exchange may be effected which allows the osmotic pressure of an aqueous solution located in one of the compartments to be modified in a controlled manner, with an aqueous solution comprising a salt being introduced into the other compartment. This type of cartridge is widely used in the medical field. According to a preferred method, a dialysis cartridge having hollow fibres is used, for example, a cartridge of this type having the following specific properties: internal diameter of the fibres of from 100 to 400 μm, total external surface-area of the fibres of from 0.3 to 2 m², length of fibres of from 10 to 40 cm, ultra-filtration coefficient of from 1.5 to 8 ml/h·mmHg.

As has been set out in detail above, the lysis procedure can be started when the temperature of the suspension in the pouch is from +1 to +8° C. According to an advantageous method, the temperature of the suspension is controlled by means of a sensor which is positioned on the external loop type circulation.

In accordance with the osmotic fragility detected, two main parameters may be adjusted, the flow rate of the erythrocyte suspension in the dialysis cartridge and the osmolarity of the lysis solution, given that it is preferable to fix, in both cases, a constant flow rate for the lysis solution. The value of the flow rate is not critical. Typically, for a dialysis cartridge having hollow fibres, as described above, the flow rate of the lysis solution is fixed at from 50 to 300 ml/min, preferably from 150 to 250 ml/min.

The lysis solution is a saline solution which is hypotonic relative to the suspension of red corpuscles. When it is fixed at a constant value, its osmolarity may typically be from 20 to 120 mOsm, preferably from 70 to 110 mOsm, for example, in the order of 90 mOsm.

By way of example, the lysis solution may comprise $Na_2HPO_4$ and/or $NaH_2PO_4$ and a sugar, such as glucose.

According to a first method, the flow rate of the erythrocyte suspension through the dialysis cartridge is adjusted whilst the flow rate and osmolarity of the lysis buffer are fixed. The higher the osmotic fragility, the more the flow rate of the suspension is increased. Typically, for a cartridge whose specifications have been indicated above, the flow rate will be caused to vary within the range from 5 to 200 ml/min, preferably from 10 to 40 ml/min.

According to a second method, the osmolarity of the lysis solution is adjusted, whilst the flow rates of the suspension and the lysis solution are fixed. The higher the osmotic fragility, the more the osmolarity of the lysis solution is increased. Typically, the osmolarity will be caused to vary within the range from 10 to 200 mOsm/l, preferably from 20 to 150 mOsm/l.

According to a third method, both the flow rate of the erythrocyte suspension through the dialysis cartridge and the osmolarity of the lysis solution are adjusted.

In accordance with the invention, one introduces one or more active ingredients intended to be incorporated in the erythrocytes. The active ingredient(s) can be present in the suspension pouch and/or introduced, preferably progressively, into the suspension circulation upstream or downstream of the dialysis cartridge. Since the volumes introduced are small, refrigeration of the active ingredient is optional.

The suspension of red corpuscles is preferably produced from a globular concentrate which is from a blood group compatible with the recipient, has had the leucocytes removed, has no pathogens detected and in particular is provided in a pouch, for example, containing 500 ml. The red corpuscles may have been irradiated when they are intended for highly immuno-deficient patients who might experience an immunological reaction of the «transplant/host» type (R. J. Davey Immunol. Invest. 1995, 24 (1-2): 143-149).

According to a particular feature of the invention, the initial globular concentrate which is used to prepare the suspension has been subjected beforehand to a processing operation which is intended to remove from the blood elements other than erythrocytes.

This type of processing, for example, washing with a saline solution in order to remove the plasma or a preservation solution, is known to the person skilled in the art.

According to a particular method, the washing is carried out in the presence of one or more active ingredients to be encapsulated.

The washing may be carried out by any conventional technique, such as the quadruple pouch or 4 pouch technique for washing red corpuscles (MacoPharma method and transfer pouch). It is also possible to use an automatic red corpuscle washing device of the COBE 2991 Cell Processor type.

According to another feature of the invention, the erythrocytes can be processed beforehand with a solution which can increase and/or homogenise the osmotic strength thereof. Such solutions are known to the person skilled in the art. For example, a solution containing L-carnitine may allow an improvement in the osmotic strength of the red corpuscles to be obtained. Other examples may include solutions of heparin, citrate-phosphate-dextrose (CPD) and mannitol.

The temperature during the lysis step is preferably maintained at from +2 to +6° C., and in a still more preferable manner in the order of +4° C.

The resealing procedure is preferably carried out by reheating the lysed suspension and addition of a hypertonic resealing solution. The resealing temperature may be from +30 to +40° C. It is preferably from +35 to +38° C., for example, approximately 37° C. The incubation may typically last for from 15 to 45 minutes.

Preferably, the suspension discharged from the dialysis cartridge and a hypertonic resealing solution are introduced, preferably continuously, into an intermediate pouch. The suspension is reheated therein and incubated at the desired temperature for a term sufficient to ensure resealing. According to a specific aspect, the intermediate pouch is placed in a heated chamber or module whose internal temperature is controlled at the selected temperature.

By way of a variant, the suspension is brought to an intermediate pouch, as well as the resealing solution. When the whole of the suspension has been collected in that pouch, it is sealed and transferred to a module which allows heating to and incubation at the desired temperature.

The suspension of resealed red corpuscles may then be subjected to one or more washing steps by means of a saline solution, in order to remove the non-sealed or badly sealed cells, residues and extracellular haemoglobin.

According to another feature, the erythrocytes are processed in a solution for preserving the erythrocytes, for example, containing L-carnitine.

The erythrocytes produced are preferably stored at a temperature of from +1 to +8° C., preferably from +2 to +6° C., typically approximately +4° C.

The final haematocrit level of the product which is ready for use is in practice from 40 to 70%.

The present invention also relates to a lysis/resealing device which can be used for carrying out the process for preparing erythrocytes in accordance with the invention, the device comprising:

a module which can be refrigerated at a temperature of from +1 to +8° C. and which comprises means for cooling and controlling the temperature, a sterile, single-use removable assembly which is configured in order to be able to be placed in the module and which comprises a dialysis cartridge which can be connected, at one side, to an inlet for lysis solution and, at the other side, to an inlet for erythrocyte suspension, means for adjusting the flow rate of the erythrocyte suspension through the lysis cartridge and/or for adjusting the osmolarity of the lysis solution, in accordance with the osmotic fragility of the erythrocytes to be processed.

In accordance with an embodiment, the removable assembly which is in itself an aspect of the invention, is a single-use kit and comprises a pouch which can contain the erythrocyte suspension and a tube which connects that pouch to the dialysis cartridge, and the module comprises a pump which can co-operate with that tube and cause the erythrocyte suspension to circulate from the pouch towards and through the cartridge, that pump optionally being connected to the means for adjusting the flow rate. The assembly allows sterility to be maintained.

According to an advantageous feature, the pouch is further provided with a loop type tube which is connected to the pouch at the two ends thereof, and the module comprises a pump which can co-operate with that tube and bring about circulation of the contents of the pouch to and from that pouch. Such a flexible pouch provided with a loop type tube and at least one inlet or outlet point constitutes an aspect of the invention per se. That pouch may comprise at least one other flexible tube which is connected to each inlet/outlet. The pouch may be associated with a pump (for example, peristaltic pump) which is arranged in order to co-operate with the loop type tube and/or a support for the pouch and optionally the pump. Such a pouch may be used for administering compositions (for example, suspension, emulsion) to humans or animals, since it is desirable to conserve a given degree of homogeneity in the composition, for example, a composition for parenteral supply.

According to another advantageous feature, a temperature probe is arranged on the loop type tube.

According to another feature, a tube for injecting the active ingredient is connected to the tube which connects the pouch to the «blood» inlet of the dialysis cartridge.

According to another feature, the dialysis cartridge is connected by a tube to a flask which can contain the lysis solution, and the refrigerated module comprises a receiving means for that flask and a pump which can co-operate with the tube in order to cause the lysis solution to circulate towards and through the dialysis cartridge.

According to a preferred feature of the invention, the cooling means and means for controlling temperature are capable of maintaining a temperature of from +2 to +6° C., preferably in the order of +4° C., in the module.

According to another feature, the «blood» outlet of the dialysis cartridge is connected to an outlet tube which opens, or which may open, outside the module. According to another feature, a tube for injecting the active ingredient is connected to that outlet tube. The outlet tube may be connected to a second pouch (intermediate pouch) which can collect the erythrocyte suspension which is discharged from the lysis as well as a resealing solution (preferably introduced by a secondary tube which opens into the outlet tube slightly upstream of the point at which it opens into the intermediate pouch). That pouch is advantageously arranged in a second module which is provided with means capable of controlling the temperature in the module at from +30 to +40° C., preferably from +35° C. to +38° C.

According to an advantageous embodiment, the single-use removable assembly comprises, in a single unit, the pouches, circulation tubes, injection tubes (provided with an injection device or a receptacle which is intended to co-operate with such a device), dialysis cartridge and preferably a flask of lysis solution.

Preferably, the removable assembly itself does not comprise specific means intended for cooling or heating. These functions are only carried out by the modules or chambers in which the two portions of the assembly are placed.

The pumps used in the process and the device of the invention are preferably peristaltic pumps (occlusion pumps); according to one embodiment, the pump which brings about the recirculation of the suspension to and from the initial pouch and the pump for circulating the lysis buffer have a constant, predetermined rotation rate, whereas the pump which conveys the suspension towards the dialysis cartridge has a rotation rate which can be adjusted in accordance with the osmotic fragility of the erythrocytes to be processed.

The active ingredient may be introduced by any suitable means, for example, a fixed-rate plunger syringe, which is optionally controlled, connected to the corresponding injection tube. By way of a variant, the plunger syringes may be replaced with peristaltic pumps.

The device comprises means for adjusting the flow rate of the erythrocyte suspension through the lysis cartridge and/or adjusting the osmolarity of the lysis solution in accordance with the osmotic fragility of the erythrocytes to be processed.

According to a feature, the flow rate adjustment means are configured to control the pump which conveys the suspension towards the dialysis cartridge. According to another alternative feature, the adjustment means are configured to control the osmolarity of a lysis solution, either in order to dilute and lower the osmolarity, or to increase that osmolarity by a suitable solute being introduced. By way of a variant, a lysis solution having an osmolarity which is adjusted relative to the osmotic fragility of the erythrocytes to be processed may optionally be introduced into the module.

According to a preferred method, the device comprises electronic means which can control the lysis process and optionally the resealing process in accordance with instructions which are input by the operator (for example, the operator directly inputs the data concerning the flow rate of the erythrocyte suspension), or in accordance with data input by the operator, with reference to the osmotic fragility (the electronic means being configured in order to establish and adjust the lysis parameters, for example, the flow rate of the erythrocyte suspension). Those electronic means are preferably connected to the temperature sensors (allowing the temperature in the modules and/or at the temperature sensor for the erythrocyte suspension to be controlled). Those means can control and operate the pumps, for example, the pressure and flow rate of the suspension through the dialysis cartridge.

The modules are preferably provided, at least at one face, with a glass surface which allows visual control of the installation, and the circulation of the solutions and suspensions.

The process and the device according to the invention may be used to incorporate a number of active ingredients, selected in particular from medicaments, vaccines, enzymes, peptides, antigens and contrast agents which are used in human or animal therapy (see, for example, C. G. Millan, J. Controlled Released 2004, 95: 27-49).

The invention also relates to the application of the process in accordance with the invention to the effective, reproducible, reliable and stable incorporation of asparaginase. The term asparaginase is intended to refer, in accordance with the invention, to any asparaginase of any origin, whether natural, synthetic, artificial or recombinant, and the derivatives incorporating it, for example, combinations of asparaginase and a polymer such as polyethylene glycol (PEG) (for example, peguilated-asparaginase or pegasparaginase, which is a type of asparaginase encapsulated in PEG; for example, ONCASPAR® which is marketed by Enzon and Medac).

According to the various possible methods, asparaginase is introduced in the initial pouch and/or in the circulation of the suspension upstream and/or downstream of the dialysis cartridge. It is preferably introduced into the circulation of the suspension upstream of the dialysis cartridge. Advantageously, the osmotic fragility is measured on the suspension containing asparaginase. The suspension is then resealed, washed, optionally has a preservative solution added to it, then is stored, preferably in a flexible pouch, ready for use.

Methods are known which allow asparaginase to be metered in the suspension, so that it is possible to adjust the suspension volume in the final pouch in order to correspond to a dose prescribed for the treatment.

According to a preferred embodiment, the initial concentrate has the leucocytes removed and/or is irradiated.

According to a specific aspect, an active ingredient is also introduced which is intended for combined treatment, for example, vincristine and/or methotrexate, and/or optionally any other active ingredient which is advantageous in addition to asparaginase.

The invention also relates to a suspension or a concentrate of erythrocytes containing asparaginase which can be obtained by carrying out the process of the invention. This suspension can be produced in a pharmaceutically acceptable saline solution (generally a standard medium for erythrocytes, a solution containing NaCl and one or more ingredients selected from glucose, dextrose, adenine and mannitol; for example, SAG-mannitol or ADsol). This solution is able to ensure the preservation of the erythrocytes and may include a preservation additive, such as L-carnitine. The erythrocytes may also contain vincristine and/or methotrexate, and/or optionally any other active ingredient which is advantageous in conjunction with asparaginase. The suspension or concentrate may be processed in order to be diluted before use. The suspension may also be processed so as to be ready for use. The final haematocrit level of the product which is ready for use is preferably from 40 to 70%.

The present invention also relates to a process for treating acute lymphoblastic leukaemias and lymphomas, by means of administration of an effective quantity of an erythrocyte suspension which contains asparaginase and which can be obtained in accordance with the process of the invention. A particular aspect of the invention comprises one or more samples of blood being taken, from a patient or one or more donors, the preparation of a concentrate of erythrocytes, the incorporation of asparaginase in accordance with the invention and the production of a batch of erythrocytes incorporating asparaginase, then the administration of the suspension to the patient, by the intravenous route. Typically, a volume of processed erythrocyte suspension is administered corresponding to from 60 to 200 units of asparaginase per kg of body weight.

The invention also relates to the use of erythrocytes which contain asparaginase and which can be obtained in accordance with the process of the invention for the preparation of a medicament or drug which is intended to treat a patient for an acute lymphoblastic leukaemia or a lymphoma. A specific aspect of the invention comprises the use of one or more units of blood which are taken from a patient or one or more donors for the preparation of a concentrate of erythrocytes, the incorporation of asparaginase in accordance with the invention and the production of a batch of erythrocytes which incorporate asparaginase, for the treatment of the patient with those erythrocytes. According to a specific method, the use is intended to produce a pouch which contains a dose, for example, a volume of processed erythrocyte suspension comprising the equivalent of from 60 to 200 units of asparaginase per kg of body weight.

The invention also relates to the application of the process according to the invention to the effective, reproducible, reliable and stable incorporation of inositol phosphate, in particular inositol hexaphosphate and inositol pentaphosphate, or the derivatives thereof. It is preferably inositol hexaphosphate.

According to the various methods possible, inositol phosphate is introduced into the initial pouch and/or into the circulation of the suspension upstream and/or downstream of the dialysis cartridge. It is preferably introduced into the initial pouch. It is advantageous to measure of osmotic fragility on the suspension containing inositol phosphate. The suspension is then lysed, resealed, washed, optionally has a preservation solution added, and is then stored, preferably in a flexible pouch, ready for use.

Methods are known which allow inositol phosphate to be metered in the suspension so that it is possible to adjust the suspension volume in the final pouch in order to correspond to a dose prescribed for treatment.

According to a preferred embodiment, the initial concentrate has the leucocytes removed and/or is irradiated.

The invention also relates to a suspension or a concentrate of erythrocytes which contain inositol phosphate, in particular inositol hexaphosphate or pentaphosphate, which can be obtained by carrying out the process of the invention. That suspension may be produced in a pharmaceutically acceptable saline solution (generally, a standard medium for erythrocytes, a solution containing NaCl and one or more ingredients selected from glucose, dextrose, adenine and mannitol; for example, SAG-mannitol or ADsol). This solution can ensure the preservation of the erythrocytes and may include a preservation additive, such as L-carnitine. That suspension or concentrate may be processed in order to be diluted before use. The suspension may also be processed so as to be ready for use. The final haematocrit level of the product which is ready for use is preferably from 40 to 70%.

The invention also relates to a method for tumoral oxygenation, in particular associated with radiotherapy, comprising the administration, to the patient, of an effective quantity of an erythrocyte suspension which incorporates inositol phosphate, in particular inositol hexaphosphate, and which can be obtained by the process of the invention. A specific aspect of the invention comprises one or more samples of blood being taken, from a patient or one or more donors, the preparation of a concentrate of erythrocytes, the incorporation of inositol phosphate, in particular inositol hexaphosphate, in accordance with the invention, and the production of a batch of erythrocytes which incorporate that compound, then the administration of the suspension to the patient by the intravenous route. Preferably, that method is associated with radiotherapy treatment and it is thus possible to administer, via the intravenous route, the processed erythrocytes continuously for all or part of the radiotherapy treatment, and preferably in addition before and/or after that treatment, for a sufficient period of time.

The method according to the invention can be used in the treatment of various cancers and in particular cancers of the lungs, prostate, rectum, cesophagus as well as brain tumours. The method is intended in particular for tumours which are weakly radio-sensitive, generally hypoxic, and in particular malignant gliomas. According to specific aspects of the invention, the method is intended for the treatment of glioblastoma and ENT (ear-nose-throat) cancers.

The present invention further relates to the use of such erythrocytes which contain inositol phosphate, in particular inositol hexaphosphate, which can be obtained in accordance with the process of the invention, for the preparation of a medicament or drug which is intended to treat a patient against a cancer of the type of those described above, in particular in association with a course of radiotherapy. A specific aspect of the invention comprises the use of one or more units of blood which are taken from a patient or one or more donors for the preparation of concentrates of erythrocytes, the incorporation of the active compound in accordance with the invention and the production of batches of erythrocytes incorporating that compound, for the treatment of the patient with those erythrocytes.

The invention also relates to a method for treating drepanocytosis or other hypoxic status comprising the administration, to the patient, of an effective quantity of an erythrocyte suspension which incorporates inositol phosphate, in particular inositol hexaphosphate, and which can be obtained by the process of the invention. A specific aspect of the invention comprises one or more samples of blood being taken, from a patient or one or more donors, the preparation of a concentrate of erythrocytes, the incorporation of inositol phosphate, in particular inositol hexaphosphate, in accordance with the invention, and the production of a batch of erythrocytes which incorporate that compound, then the administration of the suspension to the patient by the intravenous route.

The present invention further relates to the use of such erythrocytes which contain inositol phosphate, in particular inositol hexaphosphate, which can be obtained in accordance with the process of the invention, for the preparation of a medicament or drug which is intended to treat a patient with hypoxia. Hypoxia is caracterised by a low oxygen delivery to the tissues, particularly to muscle and bones. This treatment is particularly interesting to treat patient suffering of drepanocytosis. A specific aspect of the invention comprises the use of one or more units of blood which are taken from a patient or one or more donors for the preparation of concentrates of erythrocytes, the incorporation of the active compound in accordance with the invention and the production of batches of erythrocytes incorporating that compound, for the treatment of the patient with those erythrocytes.

The inositol hexaphosphate or the like incorporated in the erythrocytes leads to a diminution of the oxygen affinity of the hemoglobin. This leads to a better oxygenation of tissues and to a reduction of the hypoxy symptoms due to drepanocytosis. P50 is the $O_2$ pressure ($PO_2$) corresponding to a 50% oxygen saturation of hemoglobin. An increase of P50 by 25 mmHg leads to an increase of oxygenation of about twice (oxygenation is the difference in saturation between $PO_2$ values of 100 mmHg and 40 mmHg). Therefore, for an adult having 2000 mL of red blood cells, transfusion of a blood bag containing 200 mL of erythrocytes containing inositol hexaphosphate may lead to a rise of more than 10% of erythrocytes having an oxygenation power that is twice the normal. This leads to more than 20% increase of oxygenation which is beneficial in hypoxy individuals.

The method may comprise transfusions by a volume representing between 5 and 20%, preferably 10-15% of the erythrocytes mass of the individual, and the frequency of transfusion may be advantageously of one per month or two months.

BRIEF DESCRIPTION OF THE DRAWING FIGURES

The invention will now be described in greater detail by way of non-limiting example with reference to embodiments and the drawings, in which.

EXAMPLE 1: INSTALLATION

Figure 1:
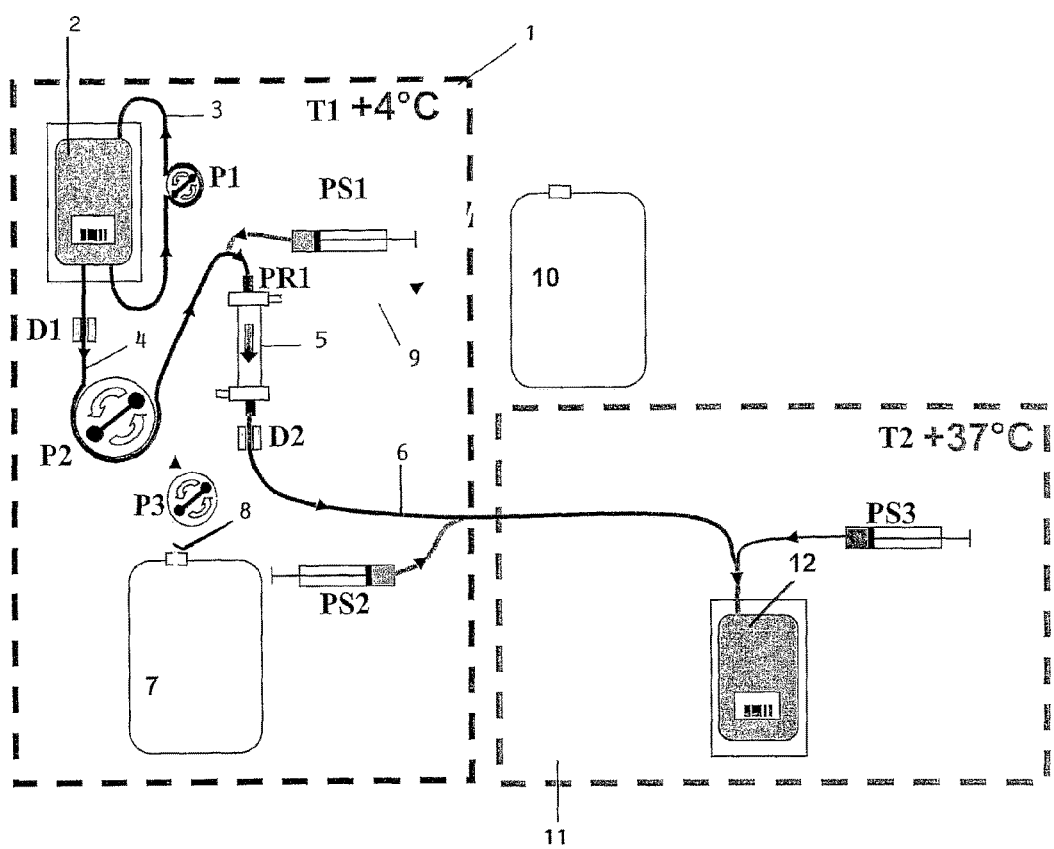
FIG. 1 is a schematic representation of a lysis/resealing device in accordance with the invention.

Reference is first made to FIG. 1. A first frame in dashed lines indicates a first module 1 which is of generally parallelepipedal form and which comprises a front face of glass, which is not illustrated, and which is formed so as to be able to be opened and closed. Peristaltic pumps P1, P2 and P3 and receiving means (not illustrated) of a removable assembly, which will now be described, are arranged on the bottom of that module. The pumps P1 and P3 have a constant, predetermined flow rate. The pump P2 is controlled in order to cause the flow rate to be varied.

The removable assembly comprises a flexible pouch 2 which contains the erythrocyte suspension to be lysed. That pouch 2 is provided with a flexible tube 3, in a loop type configuration, which co-operates with the pump P1 in order to bring about circulation to and from the pouch in order to keep the erythrocytes in suspension. The pouch is further connected, at its base, to a flexible tube 4 which is connected to the inlet of the «blood» compartment of a dialysis cartridge 5. That tube 4 co-operates with the pump P2 which brings about the circulation of the suspension from the pouch to the cartridge. A controlled plunger type syringe PS1 is connected to the tube 4 upstream of the cartridge 5, that plunger type syringe being intended to introduce an active ingredient into the circulation of erythrocytes. The outlet of the «blood» compartment of the cartridge 5 is connected to a flexible outlet tube 6 which opens outside the module 1. A second controlled plunger type syringe PS2 is connected to the tube 6, that plunger type syringe being intended to introduce an active ingredient into the circulation of lysed erythrocytes. A flask 7 which contains a lysis solution is arranged in the module 1 and is connected to the «dialysate» inlet of the cartridge 5 by a flexible tube 8 which co-operates with the pump P3 which brings about the circulation of the lysis solution through the cartridge 5. Finally, the lysis solution which is discharged from the cartridge is evacuated from the module 1 by a flexible evacuation tube 9 which opens into a flask 10 which is located outside the module 1.

The outlet tube 6 extends into a second module 11 which is generally of parallelepipedal form and which comprises a front face of glass which is not illustrated and which is formed so as to be able to be opened and closed. Means (not illustrated) for receiving elements which form part of the removable assembly are arranged on the bottom of that module. These comprise a flexible pouch 12 which is connected to the tube 6 and in which the lysed suspension is stored. A controlled plunger type syringe PS3 is connected to the tube 6 and allows the resealing product to be injected.

The removable assembly is completely produced from flexible and transparent plastics material which affords complete visibility of the process.

Figure 2:
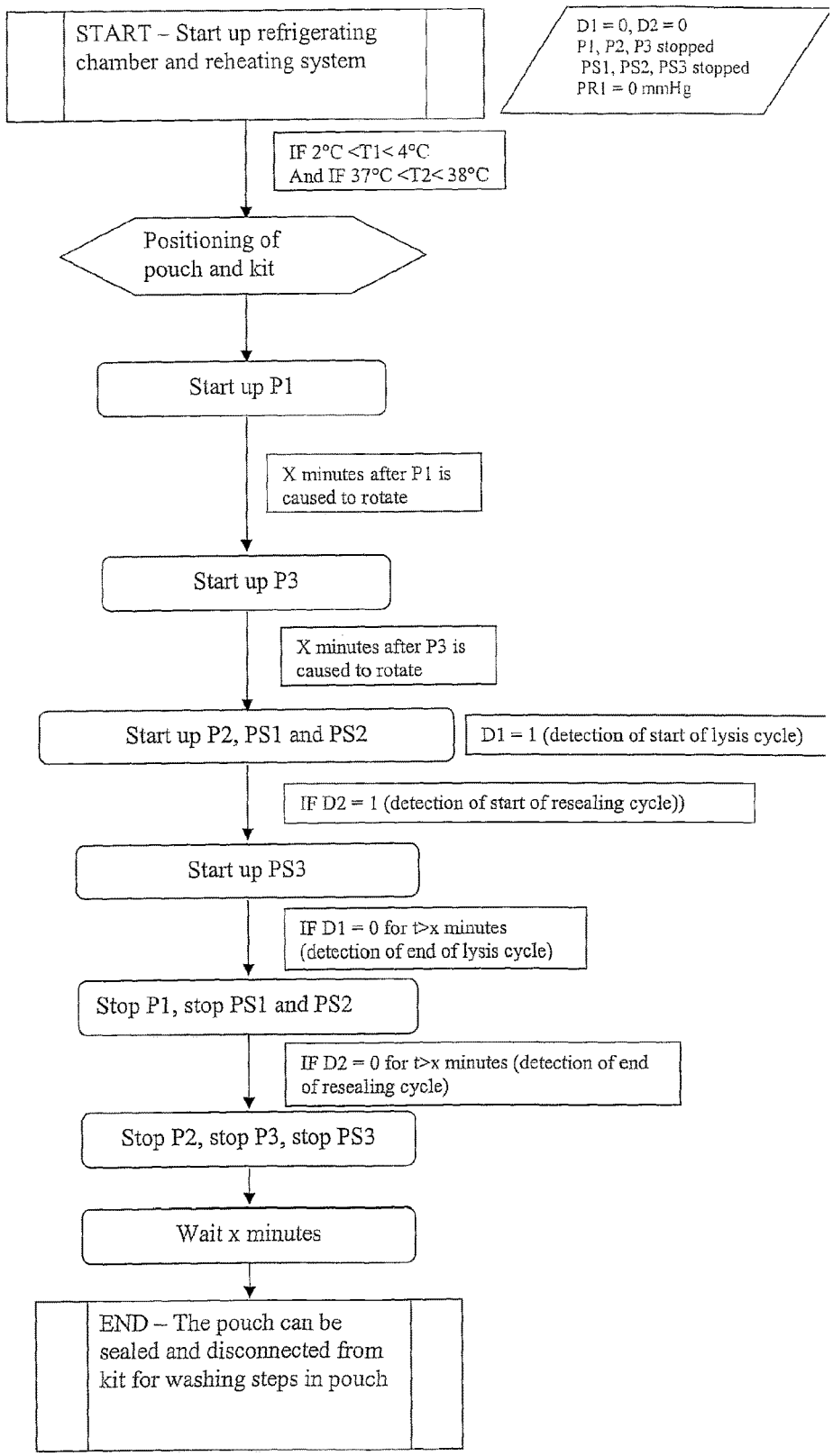
FIG. 2 is a basic flow diagram of the process.

The device is further provided with various means which are not illustrated:
  means which allow the interior of the module 1 to be cooled and the temperature therein to be controlled at from +2 to +4° C., comprising inter alia a temperature probe which is placed on the tube 3 in order to measure the temperature of the suspension which circulates therein, a temperature probe for measuring the temperature T1 inside the module 1,
  the module 11 is further provided with means which allow the interior of the module 11 to be heated and the temperature T2 therein to be controlled at from +37 to +38° C.; a temperature probe is placed inside the module,
  means for detecting (for example, ultrasound or colorimetric means) the presence of erythrocytes in the tubes at D1 and D2,
  means PR1 for measuring the pressure at the inlet of the dialysis cartridge,
  an electronic device which receives, firstly, the information from the temperature probes, pressure probes and detection means and, secondly, the information relating to the adjustments of the lysis parameters; based on those data, the device controls the pumps P1, P2 and P3. A process flow chart is illustrated in FIG. 2.

The electronic device is constituted by a computer which is designed to execute the above flow chart.

According to an additional feature, it records the parameters of each lysis procedure and therefore of each concentrate processed.

EXAMPLE 2: ENCAPSULATION OF ASPARAGINASE

In this example, the osmotic fragility is defined by the concentration of NaCl expressed in g/L bringing about 50% haemolysis.

1) Influence of Asparaginase on the Osmotic Fragility:
  a. Preparation of Asparaginase Solutions:
  2.5 ml of 0.9% NaCl were injected by means of a syringe, via the septum, into a flask which contains 10000 IU of asparaginase in powder form. The admixture was agitated until dissolved, a mother solution at a concentration of 4000 IU/ml then being obtained. The contents were removed by means of the syringe and it was placed in a 5 ml haemolysis tube. 3 solutions were prepared and stored at +4° C.: a 0 IU/ml solution (constituting a 0.9% NaCl control), a 3200 IU/ml solution (625 μl of 0.9% NaCl solution were added to the mother solution) and a 1600 IU/ml solution (1 ml of the 3200 IU/ml solution was removed, to which 1 ml of 0.9% NaCl solution was added).

b. Washing the Red Corpuscles:
    starting from whole blood which was taken over citrate phosphate dextrose and centrifuged at +4° C. for 20 minutes at 1000 g,
    the plasma was decanted and the buffycoat removed,
    0.9% NaCl was added at +4° C., volume for volume, to the concentrate of red corpuscles,
    centrifuging was carried out for 20 minutes at 1000 g, then the supernatant was removed,
    a second washing operation was carried out, then a third, by repeating both preceding steps
    the supernatant was removed and the haematocrit was adjusted to 80% with a 0.9% NaCl solution,
    tubes were prepared with a volume of suspension of red corpuscles of 875 μL.

Figure 3:
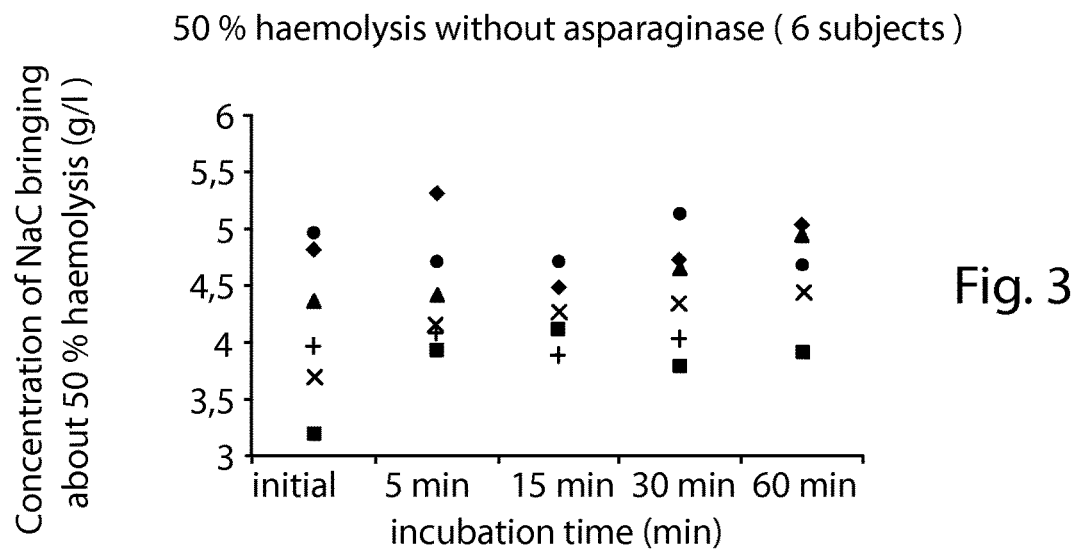
FIG. 3 is a graph showing the progress of the haemolysis of the erythrocytes, expressed as a concentration (g/L) of NaCl bringing about 50% haemolysis in accordance with the incubation time expressed in minutes.
Figure 4:
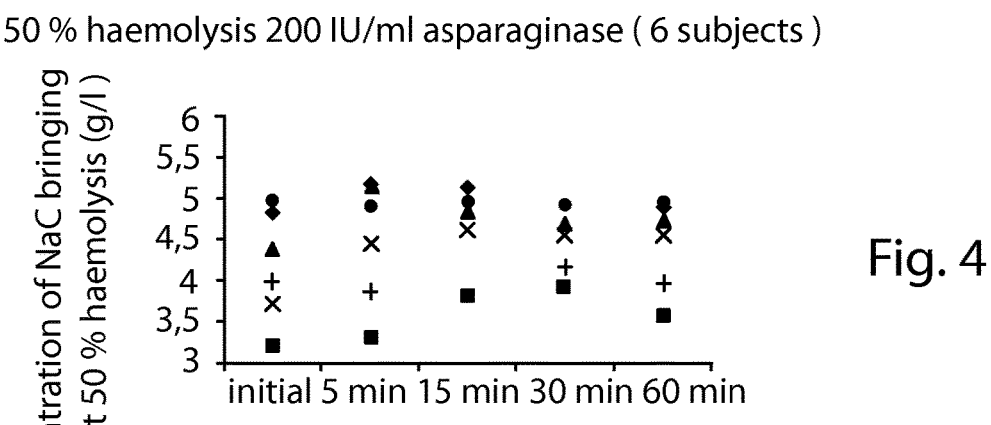
FIG. 4 is a graph similar to that of FIG. 3, the haemolysis being measured on this occasion in the presence of asparaginase (200 IU/ml)
Figure 5:
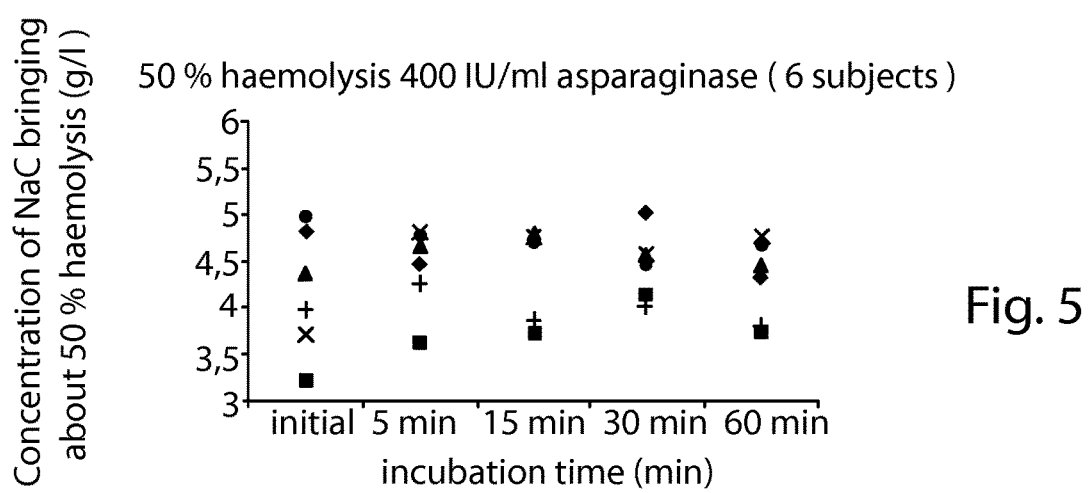
FIG. 5 is a graph similar to that of FIGS. 3 and 4, the measurement being carried out in the presence of asparaginase (400 IU/ml)

This was carried out on 6 blood samples from 6 different donors.

c. Addition of the Asparaginase Solution
    the initial osmotic fragility was measured with respect to the 6 samples,
    125 μL of 0, 1600 or 3200 IU/ml asparaginase solution were added at the rate of 6 tubes for each asparaginase concentration; each tube was gently agitated for a few moments. The final concentrations contained in the three groups of six tubes are: 0, 200 and 400 IU/ml. The tubes were stored at +4° C. on crushed ice until the osmotic fragility was measured,
    4 incubation times were tested: 5, 15, 30 and 60 minutes. The end of the incubation time is defined as the removal of the tube from the crushed ice,
    the measurement of osmotic fragility is carried out at ambient temperature.

d. The measurements of osmotic fragility are carried out on the device marketed by SODEREL MEDICAL, Haillecourt, France, under the name OSMOCELLS®.

e. Results
  The development and dispersion of the osmotic fragility of the erythrocytes before dialysis, in the absence or in the presence of asparaginase, are set out in FIGS. 3, 4 and 5.

These results demonstrate a wide variability of the osmotic fragility of the erythrocytes from one blood sample to the next, in accordance with the concentration of asparaginase present and in accordance with time. These results emphasise the importance of measuring the osmotic fragility on the erythrocyte sample to be processed, as close as possible to the dialysis phase, and preferably in the presence of the asparaginase to be encapsulated.

2) Encapsulation and Resealing Process:
  a. Equipment
  Dialysis Cartridge:
  PRISMA M60 PPI model marketed by GAMBRO, Lakewood, Colo., USA
  dimensions (cm): 38×21×9
  blood chamber volume: 84 ml
  hollow fibres: acrylonitrile and sodium methallyl sulphonate copolymer
  effective surface-area: 0.60 m$^2$
  Operating Parameters of the Installation:
  P1=20 ml/min
  P2=variable
  P3=150 ml/min
  PS3=10% of P2
  T2=30 min.
  b. Products packed red blood cells provided by "Centre de Transfusion Sanguine" (French Blood Transfusion Centre), that is to say, red cells in suspension in SAG-mannitol, adjustment of the haematocrit to 70% asparaginase solution: used to have 400 IU per ml of suspension of red corpuscles before dialysis.

to the invention (with P2 adjusted in accordance with table 1 say depending on the osmotic fragility of each sample) have also been followed, and those haematological parameters were compared to the values obtained for a healthy individual. The means of the hematological parameters measured are presented in Table 2.

TABLE 2

| Haematological parameters | Initial cell material | End product (J0) | End product after + 24 h at + 4° C. | Norm values (circulating cells) |
|---|---|---|---|---|
| Mean Cell Volume (MCV) (femto liter) | 84.7 ± 2.9 | 76.6 ± 3.9 | 80 ± 3.7 | 83-97 |
| Mean Cell Haemoglobin (pg) | 28.4 ± 1.7 | 22.1 ± 0.7 | 22.5 ± 1.6 | 28-32 |
| Mean Cell Haemoglobin Concentration (%) | 34.0 ± 1.2 | 29.2 ± 0.9 | 27.9 ± 1.2 | 31-35 |
| Osmotic fragility (Salinity inducing about 50% haemolysis) (g/l) | 3.97 ± 0.5 | 3.53 ± 0.4 | Not carried out | 3.7-4.3 |
| Haematocrit of the suspension (%) | 60.5 ± 3 | 50.4 ± 2.6 | 47.6 ± 3 | NA |
| Concentration of haemoglobin of the suspension (g/dl) | 18.7 ± 1.1 | 12.9 ± 0.7 | 13.1 ± 0.6 | NA |
| Concentration of erythrocytes ($10^6/mm^3$) | 6.31 ± 0.44 | 5.8 ± 0.44 | 5.8 ± 0.37 | NA |
| Extracellular Haemoglobin (g/dL) | 0 | 0 | 1 | NA |

NA = not applicable c. Results

Figure 6:
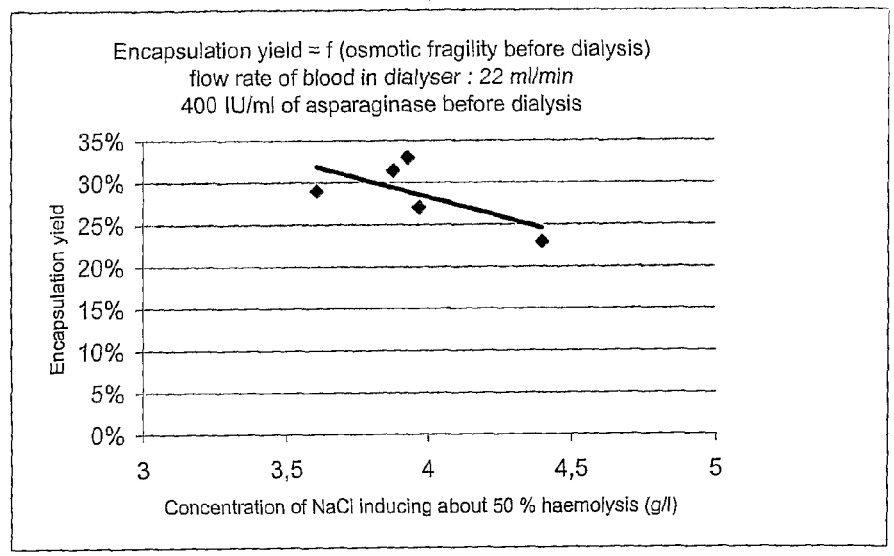
FIG. 6 is a graph showing the encapsulation yield in accordance with the concentration in g/L of NaCl bringing about 50% haemolysis.

FIG. 6 shows the encapsulation yield in the case of 400 IU/ml asparaginase with a flow rate P2 of 22 ml/min in the dialyser. It appears that the encapsulation yield varies in accordance with the osmotic fragility before dialysis (5 samples). Optimisation of the process of the invention is brought about by the dialysis parameters being adjusted, and in particular the flow rate of the erythrocyte suspension in the dialyser, in accordance with the osmotic fragility measured, so as to ensure an encapsulation yield which is as constant as possible in spite of the variability inherent in the blood samples.

With the flow rate P2 (flow rate of the erythrocyte suspension in the dialysis cartridge) being taken as the adjustment means, it was possible to establish the following optimum levels for the dialysis cartridge used.

TABLE 1

| Osmotic fragility g/L | FLOW RATE P2 ml/min |
|---|---|
| >4.7 | 24 |
| 4 to 4.7 | 25 |
| 3.5 to 4 | 22 |
| <3.5 | 20 |

The reduction in the flow rate P2 for an osmotic fragility >4.7 is explained by phenomena resulting from dialysis. The increase in the trans-membranous pressure for flow rates in the order of 26 ml/min and above brings about an increase in the osmosis effect. Therefore, it is advantageous to decrease the flow rate P2, as indicated.

Haematological and incorporation parameters of 7 different erythrocyte samples processed by the process according Incorporation Parameters:

Dosage of asparaginase is made on the erythrocytes after lysis through freezing-thawing, using the method described in J. L. Orsonneau, Annales de Biologie Clinique 2004, vol. 62, No. 5.

Mean globular level of asparaginase expressed in IU of asparaginase per $10^9$ erythrocytes: 10±1.1.

Mean corpuscular concentration of asparaginase expressed in IU/ml of erythrocytes: 112±11.3.

Encapsulation yield (corpuscular concentration of asparaginase in the end product/concentration of asparaginase before dialysis): 29.8%±2.1.

In preliminary tests carried out on 14 different samples without taking into account the osmotic fragility and without the flow rate being adjusted, but with flow rates P2 of from 18 to 30 ml/min, it was possible to measure a mean encapsulation yield of from 32±12.4%, which represents an excessively wide variability. On the contrary, the adjustment of the flow rate P2 in the above experiment allowed to obtain a much more homogenous mean encapsulation yield (29.8%±2.1).

What is claimed is:

1. A lysis and resealing device for preparing erythrocytes which contain an active ingredient, wherein the device comprises a first container and a second container, wherein the first container may be cooled and contains in its internal space a first pouch which can contain an erythrocyte suspension, the lysis device further comprising a dialysis cartridge and a first tube connecting said dialysis cartridge, at one side, to a lysis solution and a second tube connecting said dialysis cartridge, at the other side, to the first pouch, and a pump which can cooperate with said second tube and cause the erythrocyte suspension to circulate from the pouch towards and through the cartridge, wherein the first container maintains the temperature at from +1 to +8° C. in the internal space containing the first pouch, and wherein the second container contains a second pouch in its internal space and maintains the temperature at from +30 to +40° C. in the internal space containing the second pouch;

wherein the device comprises a computer which can control the lysis process and the resealing process in accordance with instructions which are input by a device operator, or in accordance with data input by the operator, with reference to the osmotic fragility, the computer being configured in order to establish and adjust the lysis parameters, selected from the flow rate of the erythrocyte suspension, the osmolarity of the lysis solution and both;

wherein said computer is connected to the temperature sensors to allow the temperature in the modules and/or at the temperature sensor for the erythrocyte suspension to be controlled; and wherein said computer controls and operates the pumps to control the pressure and flow rate of the suspension through the dialysis cartridge.

2. The lysis and resealing device of claim 1, comprising pumps P1, P2 and P3 and wherein the computer receives, firstly, information from temperature probes, pressure probes and detection devices and, secondly, information relating to the adjustments of the lysis parameters;

wherein based on said first and second information, the computer controls pumps P1, P2 and P3; and wherein pump P2 causes fluid to move from the first pouch to the dialysis cartridge, which cartridge is in fluid communication with the second pouch.

3. The lysis and resealing device of claim 2, wherein pumps P1 and P3 have a constant, predetermined flow rate and pump P2 is controlled by the computer in order to cause the flow rate to be varied.

4. The lysis and resealing device of claim 2, wherein the computer controls the temperatures of the first and second containers.

5. A lysis and resealing device for preparing erythrocytes which contain an active ingredient, wherein the device comprises a first container and a second container, wherein the first container may be cooled and contains in its internal space a first pouch which can contain an erythrocyte suspension, the lysis device further comprising a dialysis cartridge and a first tube connecting said dialysis cartridge, at one side, to a lysis solution and a second tube connecting said dialysis cartridge, at the other side, to the first pouch, and a pump which can cooperate with said second tube and cause the erythrocyte suspension to circulate from the pouch towards and through the cartridge, wherein the first container maintains the temperature at from +1 to +8° C. in the internal space containing the first pouch, wherein the device comprises an electronic device for electronically adjusting the flow rate of the erythrocyte suspension through the dialysis cartridge and/or electronically adjusting the osmolarity of the lysis solution as a function of the osmotic fragility of the erythrocytes to be processed that are present in the first pouch, said electronic device receiving instructions input into the device, or data input into the device, as a function of the osmotic fragility, wherein the second container contains a second pouch in its internal space and maintains the temperature at from +30 to +40° C. in the internal space containing the second pouch, and wherein said electronic device also controls the temperature and said pump;

wherein the device comprises a computer which can control the lysis process and the resealing process in accordance with instructions which are input by a device operator, or in accordance with data input by the operator, with reference to the osmotic fragility, the computer being configured in order to establish and adjust the lysis parameters, selected from the flow rate of the erythrocyte suspension, the osmolarity of the lysis solution and both;

wherein said computer is connected to the temperature sensors to allow the temperature in the modules and/or at the temperature sensor for the erythrocyte suspension to be controlled; and wherein said computer controls and operates the pumps to control the pressure and flow rate of the suspension through the dialysis cartridge.

6. The device according to claim 5, wherein the first pouch is provided with a tube which is connected to the first pouch at the two ends thereof and the first container comprises a pump which can co-operate with that tube and bring about circulation of the contents of the first pouch to and from said first pouch.

7. The device according to claim 5, wherein a tube for injecting the active ingredient is connected to the tube which connects the first pouch to the blood inlet of the dialysis cartridge, the cartridge is connected by a tube to a flask which can contain the lysis solution, and the first container is configured to receive said flask and a pump which can co-operate with the tube in order to cause the lysis solution to circulate towards and through the dialysis cartridge; and the blood outlet of the dialysis cartridge is connected to a tube which opens, or which may open, outside the first container.

8. The device according to claim 7, wherein the tube which opens, or which may open, outside the first container chamber is connected to the second pouch which can collect the erythrocyte suspension which is discharged from the lysis, as well as a resealing solution.

9. The device according to claim 5, wherein said pump which causes the erythrocyte suspension to circulate from the first pouch towards and through the cartridge is electronically controlled to adjust the flow rate.

10. The device according to claim 5, wherein a tube for injecting the active ingredient is connected to the rube which connects the first pouch to the erythrocyte suspension inlet of the dialysis cartridge.

11. The device according to claim 5, wherein the dialysis cartridge is connected by a tube to a flask which can contain the lysis solution, and the refrigerated first container can receive that flask and a pump which can co-operate with the tube in order to cause the lysis solution to circulate towards and through the dialysis cartridge.

12. The device according to claim 5, wherein the first container is capable of maintaining a temperature of from +2 to +6° C. in its internal space.

13. The device according to claim 5, wherein the blood outlet of the dialysis cartridge is connected to an outlet tube which opens, or which may open, outside the first container and a tube for injecting the active ingredient is connected to that outlet tube.

14. The device according to claim 5, wherein the first container is configured to control the pump which conveys the erythrocyte suspension towards the dialysis cartridge.

15. The device according to claim 5, wherein the first container is configured to control the osmolarity of a lysis solution, either in order to dilute and lower the osmolarity, or to increase that osmolarity by a suitable solute being introduced.

16. The device according to claim 5, wherein the lysis process may be controlled electronically and wherein optionally the resealing process may be controlled electronically, and wherein both processes may be controlled in accordance with instructions which are input by the operator, or in accordance with data input by the operator, with reference to the osmotic fragility.

17. The device according to claim 16, further comprising temperature sensors which allow the temperature in the first and second containers and/or at the temperature sensor for the erythrocyte suspension to be controlled.

18. The device according to claim 5, wherein said active ingredient is asparaginase.

19. The device according to claim 5, wherein said active ingredient is inositol phosphate.

* * * * *